(12) United States Patent
Kuriger

(10) Patent No.: US 7,678,580 B2
(45) Date of Patent: Mar. 16, 2010

(54) METHODS FOR USING A DIAGNOSTIC TEST STRIP FOR COLLECTING AND DETECTING AN ANALYTE IN A FLUID SAMPLE

(75) Inventor: Rex J. Kuriger, Danbury, CT (US)

(73) Assignee: Bayer Healthcare, LLC, Tarrytown, NY (US)

( * ) Notice: Subject to any disclaimer, the term of this patent is extended or adjusted under 35 U.S.C. 154(b) by 0 days.

(21) Appl. No.: 12/148,248

(22) Filed: Apr. 17, 2008

(65) Prior Publication Data

US 2008/0220461 A1   Sep. 11, 2008

Related U.S. Application Data

(62) Division of application No. 10/841,672, filed on May 10, 2004, now Pat. No. 7,374,949.

(60) Provisional application No. 60/473,720, filed on May 29, 2003.

(51) Int. Cl.
*C12Q 1/54* (2006.01)
*C12Q 1/00* (2006.01)
*A61B 5/145* (2006.01)
*A61B 5/00* (2006.01)

(52) U.S. Cl. .................. 436/180; 436/174; 436/169; 436/164; 435/14; 435/4

(58) Field of Classification Search .................. 436/180, 436/174, 164, 169; 435/14, 4
See application file for complete search history.

(56) References Cited

U.S. PATENT DOCUMENTS 2,748,769 A   6/1956   Huber ...................... 604/272
4,627,445 A   12/1986  Garcia et al. ............... 600/583

(Continued)

FOREIGN PATENT DOCUMENTS

DE   2803345   3/1979

(Continued)

OTHER PUBLICATIONS

PCT International Search Report for International Application No. PCT/US1997/22618 mailed on Jan. 1, 1998 (8 pages).

(Continued)

*Primary Examiner*—Walter D Griffin
*Assistant Examiner*—Christine T Mui
(74) *Attorney, Agent, or Firm*—Nixon Peabody LLP

(57) ABSTRACT

A test strip for use of the determination of an analyte in a fluid sample according to one embodiment of the present invention is disclosed. The test strip comprises a base having a top and a bottom, a collection chamber that extends between the top and the bottom of the base, a containing ring that is disposed on the bottom of the base and surrounds the collection chamber, and a capillary channel formed in top of the base that has an inlet fluidly coupled to the collection chamber, a test element disposed within the capillary channel. A lid is attached to the top of the base and covers the collection chamber, the test membrane, and at least a portion of the capillary channel.

20 Claims, 5 Drawing Sheets

U.S. PATENT DOCUMENTS

| | | | |
|---|---|---|---|
| 5,037,431 A | 8/1991 | Summers et al. | 606/131 |
| 5,279,294 A | 1/1994 | Anderson et al. | 600/322 |
| 5,320,607 A | 6/1994 | Ishibashi | 604/115 |
| 5,411,858 A | 5/1995 | McGeehan et al. | 435/4 |
| 5,700,695 A * | 12/1997 | Yassinzadeh et al. | 436/180 |
| 5,855,801 A | 1/1999 | Lin et al. | 216/2 |
| 5,962,215 A | 10/1999 | Douglas et al. | 435/4 |
| 5,968,765 A | 10/1999 | Grage et al. | 435/25 |
| 6,071,251 A | 6/2000 | Cunningham et al. | |
| 6,099,484 A | 8/2000 | Douglas et al. | 600/583 |
| 6,152,942 A | 11/2000 | Brenneman et al. | 606/181 |
| 6,206,841 B1 | 3/2001 | Cunningham et al. | 600/584 |
| 6,315,738 B1 | 11/2001 | Nishikawa et al. | |
| 6,379,324 B1 | 4/2002 | Gartstein et al. | 604/22 |
| 6,706,159 B2 | 3/2004 | Moerman et al. | 204/403.03 |
| 2001/0039057 A1 | 11/2001 | Douglas et al. | 436/169 |
| 2002/0130042 A1 | 9/2002 | Moerman et al. | 204/403.01 |
| 2002/0169290 A1 | 11/2002 | Bornaes et al. | 530/351 |
| 2002/0188223 A1 * | 12/2002 | Perez et al. | 600/573 |
| 2003/0031592 A1 | 2/2003 | Knappe | 422/56 |

FOREIGN PATENT DOCUMENTS

| | | |
|---|---|---|
| DE | 3708031 | 11/1987 |
| EP | 0021798 | 1/1981 |
| EP | 0212906 | 3/1987 |
| EP | 0230472 | 8/1987 |
| EP | 0254203 | 1/1988 |
| EP | 0371503 | 6/1990 |
| EP | 0449525 | 10/1991 |
| EP | 0520296 | 12/1992 |
| EP | 0575952 | 12/1993 |
| EP | 0671146 | 9/1995 |
| GB | 2222251 | 2/1990 |
| JP | 2000-116629 | 4/2000 |
| JP | 2002-168861 | 6/2002 |
| WO | WO 91/09139 | 6/1991 |
| WO | WO 92/15863 | 9/1992 |
| WO | WO 93/03673 | 3/1993 |
| WO | WO 94/09713 | 5/1994 |
| WO | WO 96/37148 | 11/1996 |
| WO | WO 98/24366 | 6/1998 |
| WO | WO 0040150 | 7/2000 |
| WO | WO 02100278 | 12/2002 |

OTHER PUBLICATIONS

PCT International Search Report for International Application No. PCT/US2002/18278 mailed on Sep. 13, 2002 (3 pages).

* cited by examiner

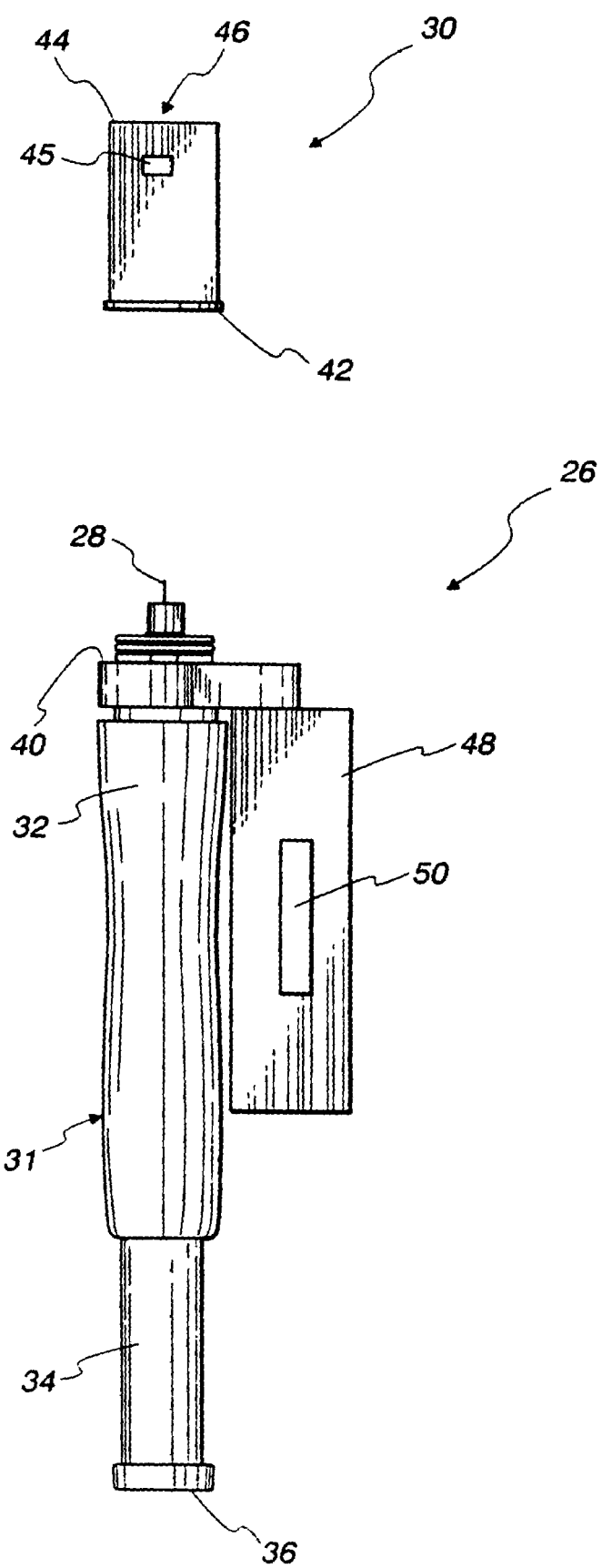

METHODS FOR USING A DIAGNOSTIC TEST STRIP FOR COLLECTING AND DETECTING AN ANALYTE IN A FLUID SAMPLE

CROSS-REFERENCE TO RELATED APPLICATION

This application is a divisional of U.S. patent application Ser. No. 10/841,672 filed May 10, 2004, now U.S. Pat. No. 7,374,949, which claims priority to Provisional Application No. 60/473,720 filed on May 29, 2003, both of which are incorporated by reference in their entirety.

FIELD OF THE INVENTION

The present invention relates generally to diagnostic instruments and, more particularly, to a diagnostic test strip for use in determining the concentration of an analyte in a liquid sample.

BACKGROUND OF THE INVENTION

Test strips (e.g., biosensors) containing reagents are often used in assays for determining the concentration of an analyte in a fluid sample. Testing and self-testing for the concentration of glucose in blood is a common use for test strips. One method of obtaining a blood sample and analyzing the sample for determining the glucose level is with a lancing device and a separate blood collection device. In obtaining a blood sample, a drop of blood is obtained from the fingertip using the lancing device, and the blood is harvested using a test strip, which is then analyzed by a test unit that determines the concentration of glucose in the blood. Test strips are also used for determining the concentration or presence of various other analytes (e.g., fructosamine, hemoglobin, cholesterol, glucose, alcohol, drugs including illegal drugs, etc.) in a variety of body fluids (e.g., blood, interstitial fluid, saliva, urine, etc.).

A drawback associated with the use of physically separate lancing and collection devices is that a patient/user must manipulate two different instruments requiring the user/patient to bring the collection device (e.g., the test strip) to the area of skin that has been lanced to collect the sample. Because the user must align the collection device with the sample to be collected, a larger than necessary amount of sample often is produced and collected to ensure an accurate analysis. In other situations, not enough sample is collected for accurate analysis because the collection device is not properly positioned. This problem can be further compounded if the user has impaired vision or poor dexterity. Because test systems are requiring smaller volumes of blood for analysis, it is difficult to position a collection instrument for proper collection.

The surface condition of the skin affects the formation of a blood droplet at the lancet site on skin. Many individuals use hand lotions, have oily or sweaty skin, or do not dry their hands completely after washing which also affects droplet formation. Often users do not always cleanse the area of skin to be lanced with alcohol. These variations increase the wettability of the skin's surface causing the droplet to spread in an uncontrolled and unpredictable manner making it difficult to harvest the sample.

Further, the collection of blood samples on alternative sites such as the forearm is complicated by the presence of body hair because the sample (e.g., blood) has a tendency to "wick up" the hairs found on these parts of the body. Cleaning the lance site with alcohol does not alleviate this wicking problem. Thus, there exists a need for a lancing and collection device that co-locates the lancet and the collection point to accurately collect a blood sample for analysis.

SUMMARY OF THE INVENTION

A test strip for use of the determination of an analyte in a fluid sample according to one embodiment of the present invention is disclosed. The test strip comprises a base having a top and a bottom, a collection chamber that extends between the top and the bottom of the base, a containing ring that is disposed on the bottom of the base and surrounds the collection chamber, and a capillary channel formed in top of the base that has an inlet fluidly coupled to the collection chamber, a test element disposed within the capillary channel. A lid is attached to the top of the base and covers the collection chamber, the test membrane, and at least a portion of the capillary channel.

The above summary of the present invention is not intended to represent each embodiment, or every aspect, of the present invention. Additional features and benefits of the present invention will become apparent from the detailed description, figures, and claims set forth below.

BRIEF DESCRIPTION OF THE DRAWINGS

FIG. 4 is a side view of a lancing and harvesting device and end cap according to another embodiment of the present invention.

Figure 1:
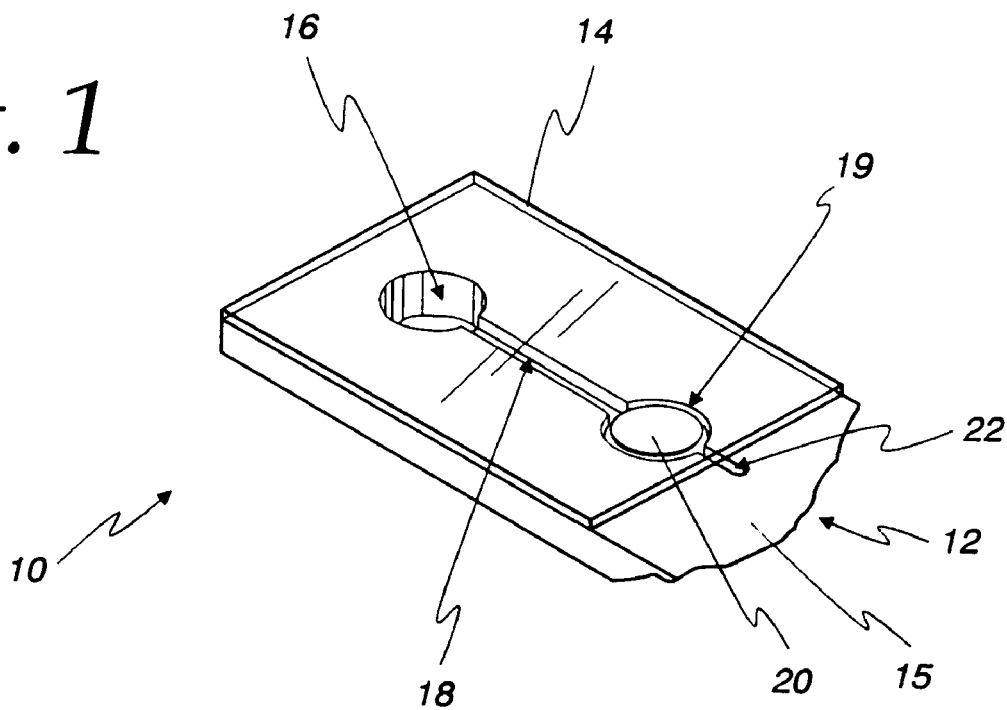
FIG. 1 is an upper perspective view of a portion of a test strip according to one embodiment of the present invention.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents and alternatives falling within the spirit and scope of the invention as defined by the appended claims.

DESCRIPTION OF ILLUSTRATED EMBODIMENTS

Figure 2:
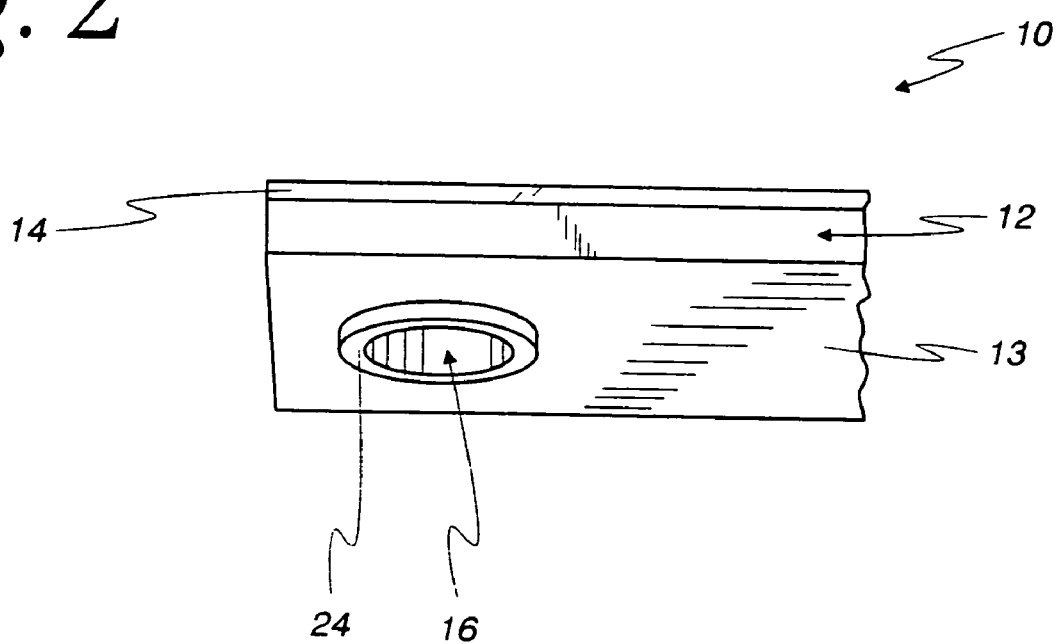
FIG. 2 is a lower perspective view of the test strip of FIG. 1.

Turning now to the drawings and initially to FIGS. 1 and 2, a test strip 10 is shown according to one embodiment of the present invention. The test strip 10 includes a base 12 and a lid 14. The base 12 has a lower surface 13 and an upper surface 15. The base 12 includes a collection chamber 16, a capillary channel 18 that includes a test area 19, and a containing ring 24. The capillary channel 18 is extended beyond the test area 19 to form an optional vent 22. The lid 14 covers the collection chamber 16 and the capillary channel 18 including the test area 19. The lid 14 is adhered to the base 12 according to one embodiment of the present invention. A test element 20, which includes a regent for use in an assay, is disposed in the test area of the capillary channel 18. The test strip 10 may be incorporated into a lancing and harvesting device 26 (FIG. 4) according to one embodiment of the present invention as will be described in detail in connection with FIGS. 4-5f.

The collection chamber 16 and the capillary channel 18, which includes the test area and the vent 22 (if any), may be embossed upon the upper surface 15 of the base 12, but may also be formed in the molding of the base 12, by machining, or through another suitable manufacturing method. In the illustrated embodiment, the collection chamber 16 is a cylindrical aperture extending through the base 12. The inlet of the capillary channel 18 is formed in the side wall of the collection chamber 16. The capillary channel 18 fluidly couples the collection chamber 16 and the test area 19 containing the test element 20. The collection chamber 16, the capillary channel 18 including the test area 19, or a combination thereof may be coated with a hydrophilic material to promote movement of the fluid sample. Additionally, according to one embodiment of the present invention, the capillary channel 18 is appropriately sized to provide under-fill protection.

In one embodiment of the present invention, a test element 20 is attached to the lid 14 with an adhesive, which is substantially clear in embodiments wherein the test element 20 is optically read through the lid 14. In embodiments where the test element 20 is adhered to the lid 14, the test area 19 of the capillary channel 18 is dimensioned to provide a slight clearance between the bottom of the test area 19 and the bottom of the test element 20 so that the fluid sample is exposed to more surface area of the test element 20. Similarly, the test area 19 of the capillary channel 18 may be dimensioned to provide for clearance around the edge of the test element 20 as is shown in FIG. 1, for example. In alternative embodiments of the present invention, the test element can be attached to the base 12.

In the collection of a body fluid sample, such as blood, from a test subject, the lower surface 13 of the base 12 is placed on the test subject's skin. A containing ring 24, which surrounds the collection chamber 16 and downwardly extends from the lower surface 13 of the base 12, contacts the test subject's skin. As will be described in detail below, the test subject's skin is punctured within the periphery of the collection chamber 16. The containing ring 24 inhibits the spreading of the sample across the skin and maintains the sample within the periphery of the collection chamber 16. The containing ring 24 is formed during the molding of the base 12, is embossed upon the lower surface 13, or is otherwise attached to the lower surface 13 of the base 12 during manufacturing.

The base 12 can be composed of any suitable material such as, for example, polycarbonate, polypropylene, polystyrene, etc. The lid 14 is constructed of any suitable material as required by the nature of the analysis to be performed. For example, if an optical analysis is desired, the lid 14 may be constructed of a substantially optically clear material such as polyethylene terephthalate (PET) or polycarbonate, for example. Alternatively, for applications where the opacity of the lid 14 is not relevant, the lid 14 may be constructed of polycarbonate, polypropylene, polystyrene, and polyethylene terephthalate (PET). The lid material is substantially nonporous so that the lid does not absorb the sample; rather, the lid directs the sample to the inlet of the capillary channel 18 as described below.

The test strip 10 may be implemented into a variety of lancing devices according to alternative embodiments of the present invention. Examples of lancing devices that may be used with various embodiments of the present invention include those described in U.S. Pat. No. 5,152,942 ("Vacuum Assisted Lancing Device"); U.S. Pat. No. 5,350,392 ("Lancing Device with Automatic Cocking"); and U.S. Pat. No. 6,364,889 ("Electronic Lancing Device"); each of which is incorporated herein by reference in its entirety. The implementation of a test strip 10 with a lancing device 26 enable the lancing device 26 to lance the skin of a test subject and to harvest the body fluid sample from the lancet site.

Figure 3:
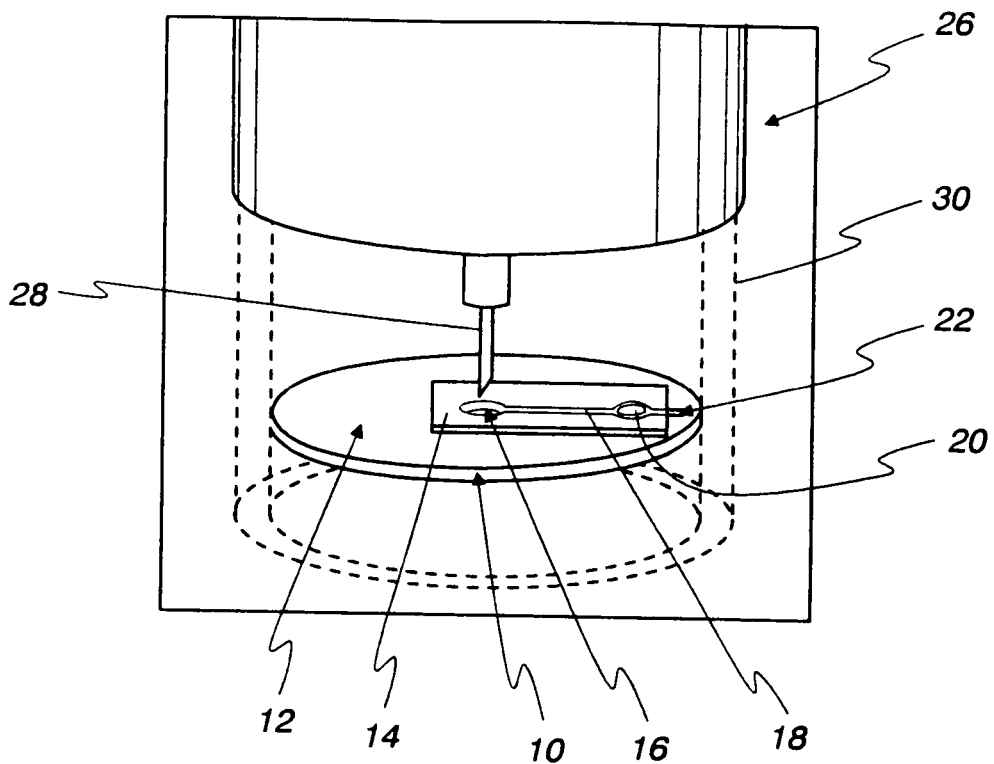
FIG. 3 is a perspective view of a test strip integrated into a lancing and harvesting device according to one embodiment of the present invention.

Referring now to FIG. 3, the forward end of a lancing and harvesting device 26 that implements a test strip 10 is shown according to one embodiment of the present invention. The test strip 10 can take on a variety of shapes and configurations to conform with numerous instrument concepts, while operating as described above. For example, while FIG. 3 shows the test strip 10 being dimensioned substantially the same as the cross-section of the end cap 30, the test strip 10 can be generally rectangular-shaped as shown in FIGS. 1-2. The test strip 10 may be attached to an end cap 30, which is removably attached to the lancing device 26. The lancing and harvesting device 26 contains a lancet 28 for puncturing both the lid 14 and the skin of the subject as is described below.

Referring now to FIG. 4, the lancing and harvesting device 26 that implements a test strip 10 is shown according to one embodiment of the present invention. The lancing assembly includes a body 32 that houses a lancing assembly 31 having a plunger 34 for driving the lancet 28. A top end 36 of the plunger 34 extends beyond the housing 32. In using the lancet 28 to puncture a test subject's skin, a user grasps the device 26 by the body 32 and depresses the top end 36 of the plunger 34—moving the plunger 34 into the body 32 of the device 26—to downwardly advance the lancet 28 into a test subject's skin. A lancet holder (not shown) is disposed within the body 32. The lancet 28 is removably attached to the lancet holder so that the lancet 28 may be detached and discarded after use. Within the housing 32, an opposite end of the lancet holder is coupled to the plunger 34. Thus, the plunger 34 moves the lancet holder which, in turn, drives the lancet 28.

The end cap 30 attaches to a forward end 40 of the device 26 opposite the plunger 34. A rim 42 of the end cap 30 removably attaches to the forward end 40 of the plunger 34. (The forward end 40 includes an O-ring according to vacuum-assisted embodiments of the lacing device 26 for forming an airtight seal between the end cap 30 and the forward end 40.) An open end 44 of the end cap 30 includes an aperture 46 through which the lancet 28 passes to puncture a test subject's skin. In one embodiment of the invention, the end cap 30 contains an aperture 45 in its sidewall for inserting and removing a test strip 10. In another embodiment of the present invention, the test strip 10 is fixedly attached to the end cap 30, which is disposable such that removing the end cap 30 also removes the used test strip 10.

During the lancing of a test subject's skin, the open end 44 of the end cap 30 is placed on an area of the test subject's skin (e.g., a forearm, a finger, etc.). The plunger 34 is depressed to advance the lancet 28 from a retracted position wherein the lancet 28 is completely contained within the end cap 30, to a lancing position wherein the lancet 28 extends through the aperture 46 in the end cap 30. Movement of the plunger 34 by the user triggers a spring (not shown) within the body 32 of the lancing assembly 31 that rapidly advances the lancet 28 into a test subject's skin. The lancing assembly 31 includes a second spring (not shown) for moving the lancet 28 back toward the retracted position.

In the embodiment shown in FIG. 4, the lancing assembly 31 further includes an instrument 48 for reading the test strip 10 (not shown) and determining the analyte concentration in the sample. The instrument 48 includes a display 50 for communicating the results of the assay to the user. In embodiments of the present invention that do not include the instrument, a separate device is used for reading the test strip 10.

According to one embodiment of the present invention, the lancing device 26 is vacuum assisted as described in U.S. Pat. No. 5,152,942 (incorporated by reference above) to facilitate the production of a blood sample at the puncture site on the test subject's skin. In such an embodiment, the rim 42 of the end cap 30 forms an airtight seal with the use of an O-ring as is described above. And an airtight seal is created between the open end 44 of the end cap 30 and the test subject's skin by pressing the end cap against the skin. The lancing assembly 31 includes a vacuum member (not shown) such as a diaphragm or bellows that displaces air within the lancing assembly and end cap 30 to form a vacuum within the end cap 30. During the lancing operation, release of the plunger 36 by the user triggers the vacuum member which evacuates air from the end cap 30.

As discussed above, the test element 20 contains a reagent for use in determining the concentration of the analyte of interest in a sample. The reagent is designed to react with the analyte in the sample. That reaction is indicative of the analyte concentration in the sample and can be measured by an appropriate sensor. The specific reagent incorporated into the test element 20 is a function of the analyte, and the type of assay to be used for determining the concentration of the analyte.

According to one embodiment of the present invention, the reagent applied to the test element 20 is designed to produce a calorimetric reaction indicative of the analyte concentration as is known in the art. An optical readhead or detector is used to measure the degree of the color change for determining the concentration of the analyte. According to one embodiment of the present invention, a light detector is disposed within the end cap 30 of the device 26 for reading the test strip. Colorimetric testing is described in detail in U.S. Pat. No. 6,181,417 B1 (entitled "Photometric Readhead with Light Shaping Plate"); U.S. Pat. No. 5,518,689 (entitled "Diffuse Light Reflectance Readhead"); and U.S. Pat. No. 5,611,999 (entitled "Diffuse Light Reflectance Readhead"); each of which is incorporated herein by reference in its entirety.

Alternatively, the reagent applied to the test element 20 is designed to produced an electrochemical reaction indicative of the analyte concentration in the sample as is known in the art. In an electrochemical assay, the regent is designed to react with the analyte to create an oxidation current at electrodes disposed within the test area 19 which is directly proportional to the concentration of glucose in the user's blood. The resulting current can be measured by a meter, such as a meter incorporated in to the instrument 48. Electrochemical testing is described in U.S. Pat. No. 5,120,420 (entitled "Biosensor and a Process for Preparation Thereof"); U.S. Pat. No. 5,660, 791 ("Fluid Testing Sensor for Use in Dispensing Instrument"); U.S. Pat. No. 5,759,364 (entitled "Electrochemical Biosensor"); and U.S. Pat. No. 5,798,031 (entitled "Electrochemical Biosensor"); each of which is incorporated herein in its entirety.

Turning now FIG. 5*a*, the operation of the lancing and harvesting device 26 will be described according to one embodiment of the present invention. The lancing and harvesting device 26 is placed against the test subject's skin S. The containing ring 24 contacts the skin S of the test subject. In an embodiment of the present invention wherein the lancing and harvesting device 26 is vacuum assisted, the vacuum is used to draw the skin S of the test subject into contact with the containing ring 24.

Figure 5A:
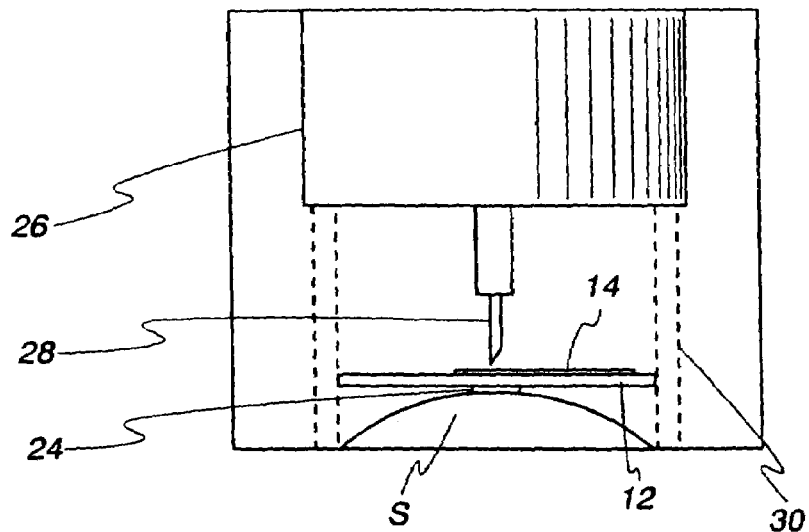
FIGS. 5a-5f are oversized perspective and side views of a forward end of a lancing and harvesting device illustrating various points during the lacing of a test subject's skin and the subsequent sample harvesting according to one embodiment of the present invention.

In FIG. 5*a*, the lancet 28 is shown just prior to lancing the skin of the test subject. In operation, the lancet 28 passes through (i.e., punctures) the lid 14 on its way the skin S of the test subject. When the skin S of the test subject is in contact with the containing ring 24, the user depresses the plunger 36 which triggers the lancing assembly 31 (FIG. 4). Upon actuation, the lancet 28 pierces the lid 14 then proceeds through the collection chamber 16 and pierces the skin S of test subject. The lance site on the test subject's skin is bounded by the collection chamber 16 (i.e., within the outer periphery of the collection chamber 16).

Figure 5B:
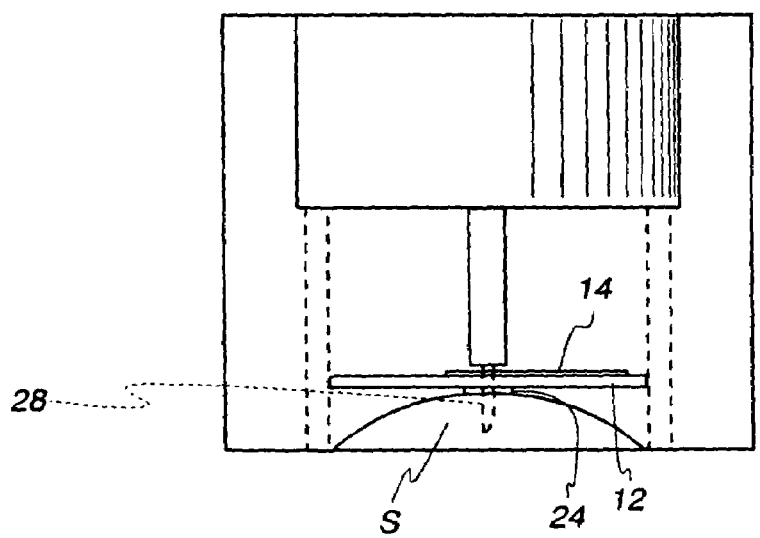
Figure 5C:
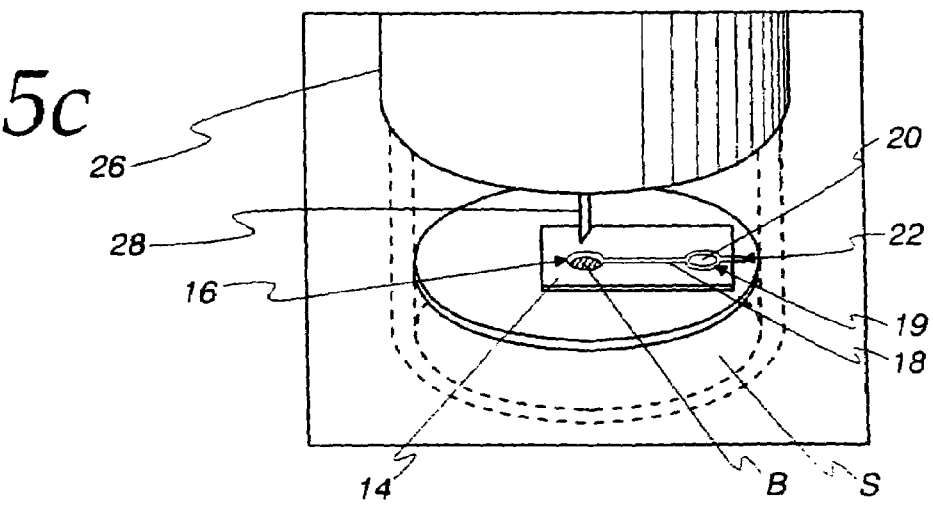
Figure 5D:
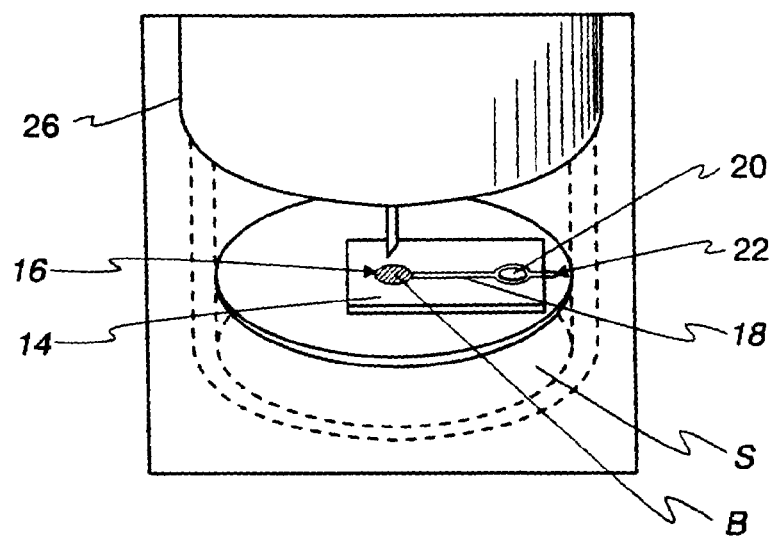

Referring now to FIG. 5*b*, the device 26 is shown after piercing the lid 14 and while puncturing the test subject's skin S. After the skin S of the test subject is pierced, the lancet 28 withdraws from the subject's skin S as shown in FIG. 5*c*. After the withdraw of the lancet 28 from the skin S, blood B begins to fill the collection chamber 16. Upon entering the collection chamber 16, some of the blood B begins to enter the capillary channel 18. As the blood B continues to fill the capillary channel 18, the blood B contacts the lid 14 as can be seen in FIG. 5*d* which directs the blood B toward the inlet of the capillary channel 18. The collection chamber 16, bounded by the containing ring 24 and the lid 14, collect and contain the blood sample B. Thus, according to one embodiment of the present invention, the harvesting of the blood sample is not dependant on any particular blood droplet formation.

Figure 5E:
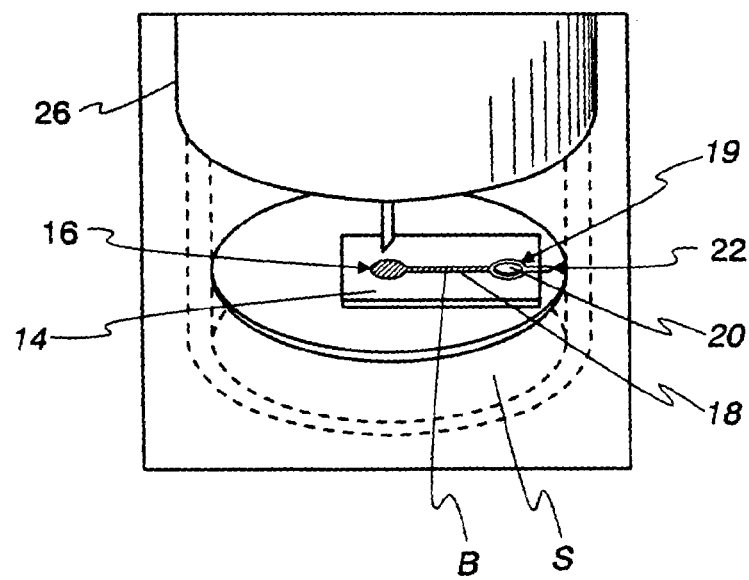

Referring now to FIG. 5*e*, upon further filling of the collection chamber 16, the blood B continues to move along the capillary channel 18 from the collection chamber 16 towards the test element 20. The blood B contacts the test element once it moves into the test area 19. According to the illustrated embodiment of the test strip 10, a vent 22 facilitates the movement of the blood B through the capillary channel 18, which allows air within the capillary channel 18 to exhaust from the channel as the blood B fills the channel 18.

Figure 5F:
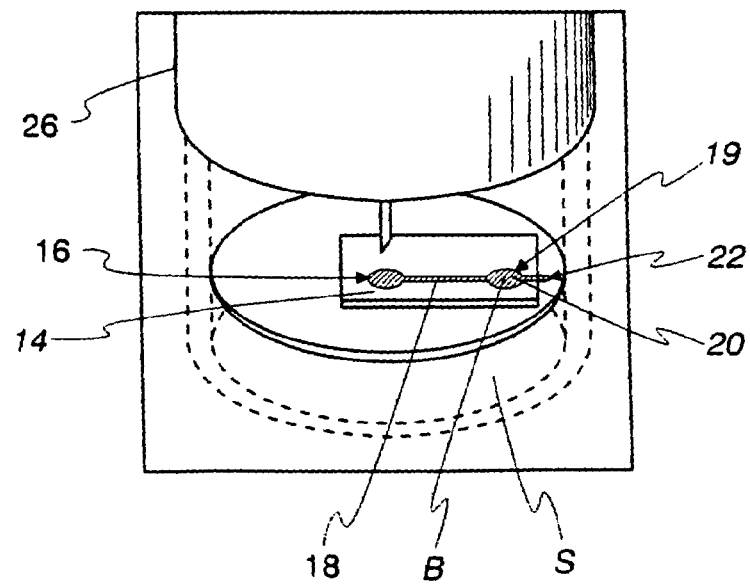

As shown in FIG. 5*f*, after reaching the end of the capillary channel 18 the blood B enters the test area 19 and contacts the test element 20, where the blood B is absorbed. The spacing along side of the test element 20 increases the exposure of the test element 20 to the blood in the reaction area, which allows for quicker absorption of the blood B by the test element 20. Further, if desired, spacing may be provided under or above the test element 20 to further facilitate rapid absorption of the blood B as is discussed above. Once the blood B is absorbed by the test element, the blood mixes with the reagent applied to the test element 20, which produces a reaction indicative of the concentration of the analyte (e.g., glucose) in the blood. If the assay is colorimetric in nature, a light sensor disposed within the end cap 30 measures the colorimetric reaction. If the assay is electrochemical in nature, a meter measures the amount of current produced by the electrochemical reaction. After use, in one embodiment, the end cap 30 and the test strip 10 may be removed from the lancing and harvesting device 26 and discarded.

Figure 6:
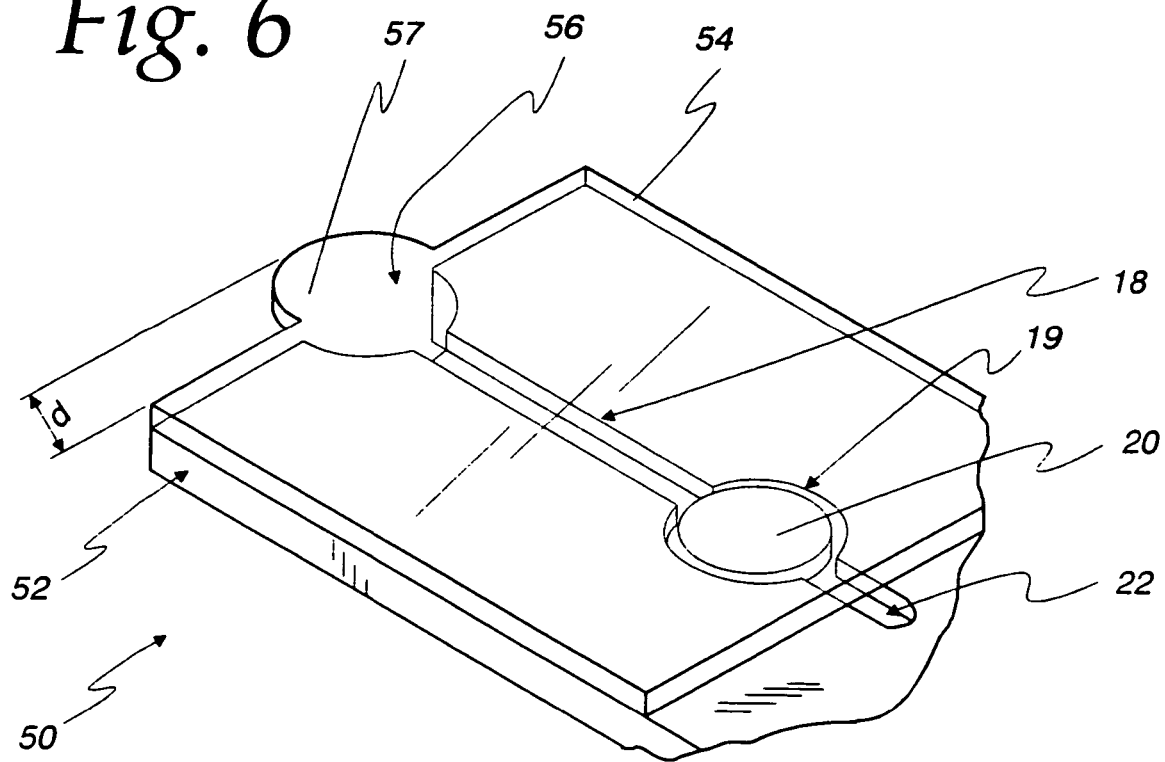
FIG. 6 is a top perspective view of a test strip according to one embodiment of the present invention.

Referring now to FIG. 6, a test strip 50 according to an alternative embodiment of the present invention is shown. The test strip 50 includes a partially enclosed collection chamber 56 that is formed at one end of a base 52 of the test strip 50. The partially enclosed collection chamber 56 may have varying degrees of closure according to alternative embodiments of the present invention. The test strip 50 includes a lid 54 having a lip 57 that extends a distanced from the lid 54. As the blood collects in the partially enclosed collection chamber 56, the blood contacts the lid 54 and lip 57 which directs the blood sample toward the inlet of the capillary channel 19.

While the test strip has been described thus far as having a two piece construction (i.e., a base 12 and a lid 14) with a capillary channel 18 formed in the base 12, the test strip 10 can have a three piece construction. In such an embodiment, a U-shaped spacer layer is disposed between the base 12 and the lid 14 and may be attached to each with an adhesive. The interior of the U-shaped spacer layer forms the side walls of a capillary channel while the lid and base form the top and bottom, respectively.

While the invention is susceptible to various modifications and alternative forms, specific embodiments thereof have been shown by way of example in the drawings and are described in detail herein. It should be understood, however, that it is not intended to limit the invention to the particular forms disclosed, but, to the contrary, the intention is to cover all modifications, equivalents and alternatives falling within the spirit and scope of the invention as defined by the appended claims.

What is claimed is:

1. A method for lancing the skin of a test subject and harvesting a body fluid sample with a lancing and harvesting device, the method comprising the acts of:
    providing a lancing and harvesting device having a test strip including a collection chamber, a containing ring surrounding the collection chamber, a capillary channel fluidly coupled to the collection chamber, a test area in fluid communication with the capillary channel, and a lid disposed over at least a portion of the collection chamber and a least a portion of the capillary channel, wherein the capillary channel extends beyond the test area to form a vent the lancing and harvesting device further including a lancet configured to puncture the lid and to extend through the collection chamber when moving between a retracted position and an extended position;
    placing the containing ring of the test strip on the skin of the test subject;
        lancing an area of the skin of the test subject bounded by the periphery of the containing ring;
    maintaining a body fluid sample produced at the lance site within the periphery of the containing ring;
    collecting the body fluid sample produced at the lance site with the test strip; and
    directing, with the lid, at least a portion of the body fluid sample from the collection chamber toward an inlet of the capillary channel.

2. The method of claim 1 further comprising measuring the concentration of an analyte in the collected body fluid sample.

3. The method of claim 2 wherein the measuring further comprises reacting the analyte in the collected body fluid sample with a reagent, the reagent being disposed on a test element received in the capillary channel of the test strip.

4. The method of claim 3, wherein the analyte is glucose.

5. The method of claim 1, wherein the test strip further comprises a test area includes a top and a bottom, the test element extending from one of the top and bottom of the test area, the test element including the reagent thereon.

6. The method of claim 5, wherein the test strip further includes a vent extending from the test area.

7. The method of claim 1, wherein the body fluid is blood.

8. A method for lancing the skin of a test subject and harvesting a body fluid sample with a lancing and harvesting device having a test strip and a lancet, the method comprising the acts of:
    placing a containing ring of the test strip on the skin of the test subject, the containing ring surrounding a collection chamber;
    puncturing a lid with a lancet, the lid being disposed over at least a portion of the collection chamber and at least a portion of a capillary channel, the capillary channel being fluidly coupled to the collection chamber;
    extending the lancet through the collection chamber;
    lancing an area of the skin of the test subject bounded by a periphery of the containing ring to form a lance site;
    maintaining the body fluid sample produced at the lance site within the periphery of the containing ring;
    collecting the body fluid sample produced at the lance site with the test strip; and
    directing, with the lid, at least a portion of the body fluid sample from the collection chamber toward an inlet of the capillary channel and a test area in fluid communication with the capillary channel, the capillary channel extending beyond the test area to form a vent.

9. The method of claim 8, further comprising measuring a concentration of an analyte in the collected body fluid sample.

10. The method of claim 9, wherein the measuring further comprises reacting the analyte in the collected body fluid sample with a reagent.

11. The method of claim 9, wherein the analyte is glucose.

12. The method of claim 8, wherein the test strip further includes a test area including a top and a bottom, the test area being in fluid communication with the capillary channel.

13. The method of claim 12, wherein the test area includes a test element extending from one of the top and bottom of the test area, the test element including a reagent thereon.

14. The method of claim 12, wherein the test strip further includes a vent extending from the test area.

15. The method of claim 8, wherein the test strip includes a base having a top and a bottom, the collection chamber extending from the bottom of the base, the containing ring being disposed on the bottom of the base.

16. A method for lancing the skin of a test subject and harvesting a body fluid sample with a lancing and harvesting device having a test strip and a lancet, the method comprising the acts of:
    placing a containing ring of the test strip on the skin of the test subject, the containing ring being disposed on a bottom of a base of the test strip and surrounding a collection chamber, the collection chamber extending from the bottom of the base;
    lancing an area of the skin of the test subject bounded by a periphery of the containing ring to form a lance site;
    maintaining a body fluid sample produced at the lance site within the periphery of the containing ring;
    collecting the body fluid sample produced at the lance site with the test strip;
    directing, with a lid, at least a portion of the body fluid sample from the collection chamber toward an inlet of a capillary channel, the lid being attached to at least a portion of a top of the base, the lid covering at least a portion of the collection chamber, the capillary channel, and a test area fluidly connected to the capillary channel, the inlet of the capillary channel being fluidly coupled to the collection chamber, the capillary channel being positioned adjacent to the top of the base, the capillary channel extending beyond the test area to form a vent;
    venting air from the test strip via a vent; and
    measuring the concentration of an analyte in the collected body fluid sample by reacting the analyte in the collected body fluid sample with a reagent.

17. The method of claim 16, further comprising, prior to the act of lancing an area of the skin, puncturing the lid with the lancet.

18. The method of claim 16, wherein the test area includes a top and a bottom, the test element extending from one of the top and bottom of the test area, the test element including a reagent thereon.

19. The method of claim 16, wherein the analyte is glucose.

20. The method of claim 16, wherein the fluid sample is blood.

* * * * *